US005688639A

United States Patent [19]

Cockerill et al.

[11] Patent Number: 5,688,639

[45] Date of Patent: Nov. 18, 1997

[54] DETECTION OF ISONIAZID RESISTENT STRAINS OF *M. TUBERCULOSIS*

[75] Inventors: Franklin R. Cockerill; Bruce C. Kline; James R. Uhl, all of Rochester, Minn.

[73] Assignee: Mayo Foundation for Medical Education and Research, Rochester, Minn.

[21] Appl. No.: 228,662

[22] Filed: Apr. 18, 1994

[51] Int. Cl.$^6$ .............................. C12Q 1/68; C12P 19/34; C07H 21/04; C07H 21/02

[52] U.S. Cl. ............................ 435/6; 435/91.1; 435/91.2; 435/86.3; 536/24.3; 536/24.33; 536/25.3; 935/76; 935/77; 935/78

[58] Field of Search ................................ 435/6, 91.2, 183, 435/91.1, 270, 94.1, 220, 863; 536/24.3, 24.33, 25.3; 936/76–78; 436/94

[56] References Cited

U.S. PATENT DOCUMENTS 4,800,159 1/1989 Mullis et al. ........................ 435/172.3

FOREIGN PATENT DOCUMENTS 9322454 11/1993 WIPO .

*Primary Examiner*—W. Gary Jones
*Assistant Examiner*—Bradley L. Sisson
*Attorney, Agent, or Firm*—Schwegman, Lundberg, Woessner & Kluth, P. A.

[57] ABSTRACT

A method for determining the susceptibility of a strain of *M. tuberculosis* to isoniazid is provided comprising employing the techniques of restriction length polymorphism analysis to determine whether or not the DNA of said strain has an NciI-MspI restriction site at the codon corresponding to codon 463 of an *M. tuberculosis* katG gene consensus sequence.

7 Claims, 7 Drawing Sheets

```
  61 AGGAATGcTGTGcCCGAGCAACACCCACCCATtACAGAaaccaccaCCGG 110
     ||||||||||||||||||||||||||||||||||||||||||||||||||
1970 AGGAATGCTGTGCCCGAGCAACACCCACCCATTACAGAAACCACCACCGG 2019

 111 AGCCgCTAgCAACGgCTGTCCCGTCGTGGGTCATATGAAATACCCCgTCG 160
     ||||||||||||||||||||||||||||||||||||||||||||||||||
2020 AGCCGCTAGCAACGGCTGTCCCGTCGTGGGTCATATGAAATACCCCGTCG 2069

 161 AGGGCGGcGGAAACCAGGACTGGTGgcCCAACCGgCTCAATCTGAAGGTA 210
     ||||||||||||||||||||||||||||||||||||||||||||||||||
2070 AGGGCGGCGGAAACCAGGACTGGTGGCCCAACCGGCTCAATCTGAAGGTA 2119

 211 CTGCACCaAAACCCGgCCGTCGCTGAcCCGATGGGTGCGGCGTTCGACTA 260
     ||||||||||||||||||||||||||||||||||||||||||||||||||
2120 CTGCACCAAAACCCGGCCGTCGCTGACCCGATGGGTGCGGCGTTCGACTA 2169

 261 TgCCgCGGAGGTCGCGACCATCGACGTTGACgCCCTGACGCGGGACATCG 310
     ||||||||||||||||||||       |||||||||||||||||||||||
2170 TGCCGCGGAGGTCGCGACCAGTCGACTTGACGCCCTGACGCGGGACATCG 2219

 311 AGGAAGTGATGACCACCTCGCAgCCGTGgTGGCCCgcCGACTACGGCCAC 360
     ||||||||||||||||||||||||||||||||||||||||||||||||||
2220 AGGAAGTGATGACCACCTCGCAGCCGTGGTGGCCCGCCGACTACGGCCAC 2269

 361 TACGGGCCGCTGTTTATCCGGATGGCGTGGCACGCTGCCGGCACCTACCG 410
     ||||||||||||||||||||||||||||||||||||||||||||||||||
2270 TACGGGCCGCTGTTTATCCGGATGGCGTGGCACGCTGCCGGCACCTACCG 2319

 411 CATCCACGACGGCCGCGGCGGCGCCGGGGGCGGCATgCAGCgGTTCGCGC 460
     ||||||||||||||||||||||||||||||||||||||||||||||||||
2320 CATCCACGACGGCCGCGGCGGCGCCGGGGGCGGCATGCAGCGGTTCGCGC 2369

 461 CGCTTAACAGCTGGCCCGACAACGCCAGCTTGGACAAGGCGCGCCGGcTG 510
     ||||||||||||||||||||||||||||||||||||||||||||||||||
2370 CGCTTAACAGCTGGCCCGACAACGCCAGCTTGGACAAGGCGCGCCGGCTG 2419

 511 CTGTGGCCGGTCAAGAAGAAGTACGGCAAGAAGCTCTCATGGGCGGACCT 560
     ||||||||||||||||||||||||||||||||||||||||||||||||||
2420 CTGTGGCCGGTCAAGAAGAAGTACGGCAAGAAGCTCTCATGGGCGGACCT 2469

 561 GATTGTTTTCgCCGgCAACTGC.GCGCT.GGAATCGATGGGCTTCAAGAC 608
     ||||||||||||||||||| || ||||| |||||||||||||||||||||
2470 GATTGTTTTCGCCGGCAACCGCTGCGCTCGGAATCGATGGGCTTCAAGAC 2519

 609 GTTCGGGTTCGGCTTCGGCCGGGTCGACCAGTGGGAGCCCGATGAGGTCT 658
     ||||||||||||||||||  | ||||||||||||||| ||||||||||||
2520 GTTCGGGTTCGGCTTCGG..GCGTCGACCAGTGGGAGACCGATGAGGTCT 2567

 659 ATTGGGGCAAGGAAGCCACcTGgCTCGGCGATGAGCGTTACAGCGGTAAG 708
     ||||||||||||||||||||||||||||||||||  |||||||| |||||
2568 ATTGGGGCAAGGAAGCCACCTGGCTCGGCGATGACGGTTACAGC.GTAAG 2616
```

FIG. 1A

```
               .         .         .         .         .
 709 CGGGATCTGGAGAACCCgCTGgCCGCGGTGcAGATGGGGCTGATCTACGT 758
     |  |||||||||||||||||||||||||||||||||||||||||||||||
2617 C..GATCTGGAGAACCCGCTGGCCGCGGTGCAGATGGGGCTGATCTACGT 2664

               .         .         .         .         .
 759 GaACCCGGAGGGGCCGAACGGCAACCCGGACCCCATGgCCGCGGCGGTCG 808
     |||||||||| |||||||||||||||||||||||||||||||||||||||
2665 GAACCCGGAGGCGCCGAACGGCAACCCGGACCCCATGGCCGCGGCGGTCG 2714

               .         .         .         .         .
 809 ACATTCGCGAGACGTTTCGGCGCATGGCCATGAaCGACGTCGAAACAgcG 858
     ||||||||||||||||||||||||||||||||||||||||||||||||||
2715 ACATTCGCGAGACGTTTCGGCGCATGGCCATGAACGACGTCGAAACAGCG 2764

               .         .         .         .         .
 859 gcgCTGATCGTcGGCGGTCACACTTTCGGTAAGACCCATGGCgCCGGCCC 908
     ||||||||||||||||||||||||||||||||||||||||||||||||||
2765 GCGCTGATCGTCGGCGGTCACACTTTCGGTAAGACCCATGGCGCCGGCCC 2814

               .         .         .         .         .
 909 GGcCGATCTGGTCGGCCCCGAACCCGAGGCTGCTCCGCTGGAGCAGATGG 958
     ||||||||||||||||||||||||||||||||||||||||||||||||||
2815 GGCCGATCTGGTCGGCCCCGAACCCGAGGCTGCTCCGCTGGAGCAGATGG 2864

               .         .         .         .         .
 959 GCTTGGGCTGGAAGAGcTCGTATGgCACCGGAACCGGTAAGGACGCGATC 1008
     ||||||||||||||||||||||||||||||||||||||||||||||||||
2865 GCTTGGGCTGGAAGAGCTCGTATGGCACCGGAACCGGTAAGGACGCGATC 2914

               .         .         .         .         .
1009 ACCAgCGGCATCGAGGTCGTATGGACGAACACCCCGACGAAATGGGACAA 1058
     ||||||||||||||||||||||||||||||||||||||||||||||||||
2915 ACCAGCGGCATCGAGGTCGTATGGACGAACACCCCGACGAAATGGGACAA 2964

               .         .         .         .         .
1059 CAGTTTCCTCGAGATCCTGTaCGGCTACGAGTGGGAGCTGACGAAGAGCC 1108
     ||||||||||||||||||||||||||||||||||||||||||||||||||
2965 CAGTTTCCTCGAGATCCTGTACGGCTACGAGTGGGAGCTGACGAAGAGCC 3014

               .         .         .         .         .
1109 CTGCTGGCGCTTGGCAATACACCGCCAAGGACGGCGCCGGTGCCGGCACC 1158
     ||||||||||||||||||||||||||||||||||||||||||||||||||
3015 CTGCTGGCGCTTGGCAATACACCGCCAAGGACGGCGCCGGTGCCGGCACC 3064

               .         .         .         .         .
1159 ATCCCGGACCCGTTCGGcGGGCCAGGGCGCTCCCCGACGATGCTGGCCAC 1208
     ||||||||||||||||||||||||||||||||||||||||||||||||||
3065 ATCCCGGACCCGTTCGGCGGGCCAGGGCGCTCCCCGACGATGCTGGCCAC 3114

               .         .         .         .         .
1209 TGACCTCTCGCTGCGGGTGGATCCGATCTATGAGCGGATCACGCGTCGCT 1258
     ||||||||||||||||||||||||||||||||||||||||||||||||||
3115 TGACCTCTCGCTGCGGGTGGATCCGATCTATGAGCGGATCACGCGTCGCT 3164

               .         .         .         .         .
1259 GGCTGGAACACCCCGAGGAATTGGCCGACGAGTTCGCCAAGGCCTGGTAC 1308
     |||||||||||||||||||||||||||||||||||   ||||||||||||
3165 GGCTGGAACACCCCGAGGAATTGGCCGACGAGTTCCGCAAGGCCTGGTAC 3214

               .         .         .         .         .
1309 AAGCTGATCCACCGAGACATGGgTCCCGtTGcGAGATACCTTGGGcCGcT 1358
     ||||||||||||||||||||||||||||||||||||||||||||||||||
3215 AAGCTGATCCACCGAGACATGGGTCCCGTTGCGAGATACCTTGGGCCGCT 3264
```

FIG. 1B

```
                 .         .         .         .         .
1359 GGTCCCCAAGcAGACCCTGcTGTGGcAGGATCCGGTCCCTGcGGTCAGCC 1408
     |||||||||||||||||||||||||||||||||||||||||||||||| |
3265 GGTCCCCAAGCAGACCCTGCTGTGGCAGGATCCGGTCCCTGCGGTCAG.C 3313
                 .         .         .         .         .
1409 ACGAcCTCGTCGGcGAAGcCGAGATTGCCAGCCTTAAGAGCCAGATCCgG 1458
     |||||||||||||||||||  |||||||||||||||||||||||||||||
3314 ACGACCTCGTCGGCGAAGC..AGATTGCCAGCCTTAAGAGCCAGATCCGG 3361
                 .         .         .         .         .
1459 GCATCGGGATTGACTGTCTCACAGCTAGTTTCGACCGCATGGGCGGCGGC 1508
     ||||||||||||||||||||||||||||||||||||||||||||||||||
3362 GCATCGGGATTGACTGTCTCACAGCTAGTTTCGACCGCATGGGCGGCGGC 3411
                 .         .         .         .         .
1509 GTCGTCGTTCCGTGGTAGCGACAAgCGCGGcGGCGCCAACGGTGGTCGCA 1558
     ||||||||||||||||||||||||||||||||||||||||||||||||||
3412 GTCGTCGTTCCGTGGTAGCGACAAGCGCGGCGGCGCCAACGGTGGTCGCA 3461
                 .         .         .         .         .
1559 TCCgCCTGCAGCCACAAGTCGGGtGGGAGGTCAACGACCCCGACGGGGAT 1608
     ||||||||||||||||||||||||||||||||||||||||||||  ||||
3462 TCCGCCTGCAGCCACAAGTCGGGTGGGAGGTCAACGACCCCGAC..GGAT 3509
                 .         .         .         .         .
1609 CTGCGCAAGGTCATTCGCACCCTGGAAGAGATCCAGGAGTCATTCAACTC 1658
     ||||||||||||||||||||||| ||||||||||||||||||||||
3510 CTGCGCAAGGTCATTCGCACCCT.GAAGAGATCCAGGAGTCATTCA.... 3554
                 .         .         .         .         .
1659 CGCGGCgCCGGGGAACATCAAAGTGTCCTTCGCCGACCTCGTCGTGCTCG 1708
     | ||||||  ||||||||||||||||||||||||||||||||||||||||
3555 CTCGGCGC..GGGAACATCAAAGTGTCCTTCGCCGACCTCGTCGTGCTCG 3602
                 .         .         .         .         .
1709 GTGGCTGTGcCgCCATAGAGAAAGCAgCAAAGGCGGCTGGCCACAACATC 1758
     ||||||||||  |   ||||||||||||||||||||||||||||||||||
3603 GTGGCTGTGCGCCACTAGAGAAAGCAGCAAAGGCGGCTGGCCACAACATC 3652
                 .         .         .         .         .
1759 ACGGTgCCCTTCACCCCGGGCCGcACGGATGCgTCGCAGGAACAAACCGA 1808
     ||||||||||||||||||||||     |||||||||||||||||||||||
3653 ACGGTGCCCTTCACCCCGGGCCCGCACGATGCGTCGCAGGAACAAACCGA 3702
                 .         .         .         .         .
1809 CGTGGAATCCTTTGCCGTGCTGGAGcCCAAGGCAGATGGCTTCCGAAACT 1858
     ||||||||||||||||||||||||||||||||||||||||||||||||||
3703 CGTGGAATCCTTTGCCGTGCTGGAGCCCAAGGCAGATGGCTTCCGAAACT 3752
                 .         .         .         .         .
1859 ACCTCGGAAAGGGCAACCCGTTGCCGGCCGAGTACAT.gCTgcTCGACAA 1907
     |||||||||||||||| |||||||||||||||||||| |||||||||||
3753 ACCTCGGAAAGGGCAA.CCGTTGCCGGCCGAGTACATCGCTGCTCGACAA 3801
                 .         .         .         .         .
1908 GGCGAACCTGCTTACGCTCAGTgCCCCTGAGATGACGGTGCTGGTAGGTG 1957
     ||||||||||||||||||||||||||||||||||||||||||||||||||
3802 GGCGAACCTGCTTACGCTCAGTGCCCCTGAGATGACGGTGCTGGTAGGTG 3851
                 .         .         .         .         .
1958 GCCTGCGCGTCCTCGG.GCAAACTACAAGcGCTTACCGCTGGGCGTgTTC 2006
     |||||||||||||||| |||||||||||||||||||||||||||||||||
3852 GCCTGCGCGTCCTCGGCGCAAACTACAAGCGCTTACCGCTGGGCGTGTTC 3901
```

FIG. 1C

```
              .         .         .         .         .
2007 ACCGAGGCCTCCGAGTCACTGACCAACGACTTCTTCGTGAACCTGCTCGA 2056
     ||||||||||||||||||||||||||||||||||||||||||||||||||
3902 ACCGAGGCCTCCGAGTCACTGACCAACGACTTCTTCGTGAACCTGCTCGA 3951

              .         .         .         .         .
2057 CATGGGTATCACCTGGGAGCCCTCGCCAGCAGATGaCGGgACCTACCAGG 2106
     ||||||||||||||||||||||||||||||||||||||||||||||||||
3952 CATGGGTATCACCTGGGAGCCCTCGCCAGCAGATGACGGGACCTACCAGG 4001

              .         .         .         .         .
2107 GcAAGGATGGCAGTgGCAAGGTGAAGTGGACCGGcAGCCGCGTGGACCTG 2156
     ||||||||||||||||||||||||||||||||||||||||||||||||||
4002 GCAAGGATGGCAGTGGCAAGGTGAAGTGGACCGGCAGCCGCGTGGACCTG 4051

              .         .         .         .         .
2157 gTCTTCGGgtCCAACTCGGAGTTGCGGGCGCTTGTCGAGGTCTATGGCGC 2206
     ||||||||||||||||||||||||||||||||||||||||||||| ||||
4052 GTCTTCGGGTCCAACTCGGAGTTGCGGGCGCTTGTCGAGGTCTAT.GCGC 4100

              .         .         .         .         .
2207 CGATGACGC.GCAGCCGAAGTTCGTGCAGGACTTCGTCGCTGCCTGGgAC 2255
     ||||||||| |||| |||||||||||   |  ||||||||||| ||||||
4101 CGATGACGCGGCAGGCGAAGTTCGTGACAGGATTCGTCGCTGCGTGGGAC 4150

              .         .         .     ▼   .
2256 AAGGTGATGAACCTCGACAGGTTCGACGTgCGCTGATTCG 2295
     ||||||||||||||||||||||||||||||||||||||||
4151 AAGGTGATGAACCTCGACAGGTTCGACGTGCGCTGATTCG 4190
```

FIG. 1D

| | | | | | |
|---|---|---|---|---|---|
| N | | 11 | 21 | 31 | 41 |
| 1 | VPEQHPPITE | TTTGAASNGC | PVVGHMKYPV | EGGGNQDWWP | NRLNLKVLHQ |
| N | | 61 | 71 | 81 | 91 |
| 51 | NPAVADPMGA | AFDYAAEVAT | IDVDALTRDI | EEVMTTSQPW | WPADYGHYGP |
| N | | 11 | 21 | 31 | 41 |
| 101 | LFIRMAWHAA | GTYRIHDGRG | GAGGGMQRFA | PLNSWPDNAS | LDKARRLLWP |
| N | | 61 | 71 | 81 | 91 |
| 151 | VKKKYGKKLS | WADLIVFAGN | CALESMGFKT | FGFGFGRVDQ | WEPDEVYWGK |
| N | | 11 | 21 | 31 | 41 |
| 201 | EATWLGDERY | SGKRDLENPL | AAVQMGLIYV | NPEGPNGNPD | PMAAAVDIRE |
| N | | 61 | 71 | 81 | 91 |
| 251 | TFRRMAMNDV | ETAALIVGGH | TFGKTHGAGP | ADLVGPEPEA | APLEQMGLGW |
| N | | 11 | 21 | 31 | 41 |
| 301 | KSSYGTGTGK | DAITSGIEVV | WTNTPTKWDN | SFLEILYGYE | WELTKSPAGA |
| N | | 61 | 71 | 81 | 91 |
| 351 | WQYTAKDGAG | AGTIPDPFGG | PGRSPTMLAT | DLSLRVDPIY | ERITRRWLEH |
| N | | 11 | 21 | 31 | 41 |
| 401 | PEELADEFAK | AWYKLIHRDM | GPVARYLGPL | VPKQTLLWQD | PVPAVSHDLV |
| N | | 61 | 71 | 81 | 91 |
| 451 | GEAEIASLKS | QIRASGLTVS | QLVSTAWAAA | SSFRGSDKRG | GANGGRIRLQ |
| N | | 11 | 21 | 31 | 41 |
| 501 | PQVGWEVNDP | DGDLRKVIRT | LEEIQESFNS | AAPGNIKVSF | ADLVVLGGCA |
| N | | 61 | 71 | 81 | 91 |
| 551 | AIEKAAKAAG | HNITVPFTPG | RTDASQEQTD | VESFAVLEPK | ADGFRNYLGK |
| N | | 11 | 21 | 31 | 41 |
| 601 | GNPLPAEYML | LDKANLLTLS | APEMTVLVGG | LRVLGANYKR | LPLGVFTEAS |
| N | | 61 | 71 | 81 | 91 |
| 651 | ESLTNDFFVN | LLDMGITWEP | SPADDGTYQG | KDGSGKVKWT | GSRVDLVFGS |
| N | | 11 | 21 | 31 | 41 |
| 701 | NSELRALVEV | YGADDAQPKF | VQDFVAAWDK | VMNLDRFDVR | & |

FIG. 2

DETECTION OF ISONIAZID RESISTENT STRAINS OF *M. TUBERCULOSIS*

BACKGROUND OF THE INVENTION

Despite more than a century of research since the discovery of *Mycobacterium tuberculosis*, the aetiological agent of tuberculosis, this disease remains one of the major causes of human morbidity and mortality. There are an estimated 3 million deaths annually attributable to tuberculosis (see, D. Snider, *Rev. Inf. Dis.*, S335 (1989)), and although the majority of these are in developing countries, the disease is assuming renewed importance in the West due to the increasing number of homeless people and the impact the AIDS epidemic (see, R. E. Chaisson et al., *Am. Res. Resp. Dis.*, 23, 56 (1987); D. E. Snider, Jr. et al., *New Engl. J. Med.*, 326, 703 (1992); M. A. Fischl et al., *Ann. Int. Med.*, 117, 177 (1992) and ibid. at 184.

Isonicotinic acid hydrazide or isoniazid (INH) has been used in the treatment of tuberculosis for the last forty years due to its exquisite potency against the members of the "tuberculosis" groups—*Mycobacterium tuberculosis, M. bovis* and *M. africanum* (G. Middlebrook, *Am. Rev. Tuberc.*, 69, 471(1952) and J. Youatt, *Am. Rev. Resp. Dis.*, 99, 729 (1969)). Neither the precise target of the drug, nor its made of action are known, but INH treatment results in the perturbation of several metabolic pathways of the bacterium. However, shortly after its introduction, INH-resistant isolates of *Mycobacterium tuberculosis* emerged. See M. L. Pearson et al., *Ann. Int. Med*, 117, 191 (1992) and S. W. Dooley et al., *Ann Int. Meal*, 117, 257 (1992).

Several investigators have associated the toxicity of INH for mycobacteri with endogenous catalase activity. See, for example, "Isonicotinic acid hydrazide," in F. E. Hahn, *Mechanism of Action of Antibacterial Agents*, Springer-Verlag (1979) at pages 98–119. This relationship was strengthened by a recent report by Ying Zhang and colleagues in *Nature*, 358, 591 (1992) which described the restoration of INH susceptibility in an INH resistant *Mycobacterium smegmatis* strain after transformation using the catalase-peroxide (katG) gene from an INH sensitive *M. tuberculosis* strain. In a follow-up study, Zhang and colleagues in *Molec. Microbial.*, 8, 521 (1993) demonstrated the restoration of INH susceptibility in INH resistant *M. tuberculosis* strains after transformation by the functional katG gene. As reported by B. Heym et al., *J. Bacteriol.*, 175, 4255 (1993), the katG gene encodes for a 80,000-dalton protein.

A significant problem in control of multiple drug resistant tuberculosis (MDR-TB) epidemics has been the delay in the detection of drug resistance. Currently laboratory methods used to identify *M. tuberculosis* drug resistance require weeks to months for results. The rapid detection of *M. tuberculosis* directly from clinical samples has been possible recently by virtue of the availability of polymerase chain reaction (PCR) and the recognition of diagnostic sequences amplified by the appropriate primers. The ability to conduct PCR analyses depends on having a high enough gene or gene product concentration so that the molecular tools work efficiently even when the organism numbers are low. Thus, the most efficient molecular assays used to detect *M. tuberculosis* depend on the IS6110 insertion sequence (about 10 copies) or the 16S ribosomal RNA (thousands of copies). See, respectively, K. D. Eisenach et al., *J. Infect. Dis.*, 61, 997 (1990) and N. Miller et al., *Abstracts ASM*, Atlanta, Ga. (1993) at page 177. Recently, B. Heym et al. (PCT WO 93/22454) disclose the use of polymerase chain reaction to amplify portions of the katG gene of putative resistant strains. The PCR products were evaluated by single-strand conformation polymorphism (SSCP) analysis, wherein abnormal strand motility on a gel is associated with mutational events in the gene. For example, in five strains, a single base difference was found in a 200 bp sequence, a G to T transversion at position 3360.This difference would result in the substitution of Arg-461 by Leu. However, carrying out SSCP on a given clinical sample can be a laborious procedure that requires sequencing to conform whether mutatiom or deletions predictive of drug resistance are in fact present in the target gene.

There is a continuing need in the art to develop a simple test permitting the rapid identification of INH-resistant strains of *M. tuberculosis.*

SUMMARY OF THE INVENTION

The present invention provides a method to rapidly identify strains of *M. tuberculosis* which are resistant to isoniazid (INH). The method is based on the identification of an NciI-MspI restriction site in codon 463 of a consensus sequence determined for the katG gene of *M. tuberculosis* which is absent in the corresponding codon in a number of INH resistant strains. The determination is preferably made by employing the techniques of restriction length polymorphism analysis. Therefore, in one embodiment, the present assay comprises the steps of:

(a) amplifying a portion of the katG gene of an *M. tuberculosis* isolate to yield a detectable amount of DNA comprising a plurality of NciI-MspI restriction sites;

(b) cleaving the DNA with a restriction endonuclease at said sites to yield DNA fragments; and (c) employing the techniques of gel electrophoresis to determine whether the number and location of the fragments is indicative of the absence of an NciI-MspI restriction site in codon 463 of said katG gene, wherein said absence is indicative of an INH-resistant swain of *M. tuberculosis.*

More specifically, gel electrophoresis is employed to compare the number and location of the DNA fragments to the number and location of DNA fragments derived from cleavage of DNA derived from an equivalent portion of the katG gene wherein the NciI-MspI restriction site at codon 463 is present, wherein a determination of the absence of the restriction site at codon 463 in the katG gene is indicative of an INH resistant swain of *M. tuberculosis.*

Preferably, the control DNA sequence of the portion of the katG gene wherein the codon 463 restriction site is present corresponds to a portion of SEQ ID NO:1 (FIG. 1, upper sequence). As discussed below, such a portion of DNA can be derived from strain H37Rv MC. The assay of step (c) also preferably includes negative control DNA fragments derived from an INH resistant strain which does not include the codon 463 NciI-MspI restriction site in the katG gene.

The term "equivalent" is defined herein to mean that any two portions of the katG gene would comprise the same number of NciI-MspI sites if the portions both were selected from a portion of the DNA of SEQ ID NO:1, and that the portions do not differ in size before cleavage to the extent that the number of fragments obtained cannot be compared following side-by-side gel electrophoresis and visualization of the resultant fragments, as described hereinbelow. Preferably, the control DNA for step (c) comprises five NciI-MspI restriction sites in each DNA molecule prior to cleavage, and the DNA of step (a) comprises four NciI-MspI restriction sites in each DNA molecule, prior to cleavage. Preferably, the portion of the katG locus which is amplified is a minor portion of the entire katG gene, i.e., about 40–70%, and is isolated and amplified by polymerase chain reaction, as described hereinbelow. The term "location" refers to the Rf of a given fragment on the gel.

The present invention also provides oligonucleotides useful in pairs as primers to initiate the polymerase chain reaction (PCR). PCR is useful both to amplify katG DNA so as to prepare both the target DNA of step (a) of the present process, as well as the DNA which is used to prepare the control digest of step (c).

The present invention also provides isolated, purified DNA corresponding to the consensus sequence derived for *M. tuberculosis* katG gene. This DNA was found to occur in nature as the katG gene of *M. tuberculosis* strain H37Rv MC, as maintained at the Mayo Clinic. The present invention also includes isolated, purified DNA encoding the consensus amino acid sequence encoded by the consensus katG DNA, as well as equivalent DNA sequences which also encode this amino acid sequence (a consensus catalase peroxidase polypeptide) and will provide the isolated, purified polypeptide corresponding to the consensus amino acid sequence.

This polypeptide can be prepared by expression by bacteria, yeast or insect cells transformed with the DNA sequences of the present invention, operatively linked to regulatory regions functional in the transformed host cells. The polypeptide can be used as a standard *M. tuberculosis* catalase peroxidase, to correlate enzymatic activity (relative level, loss and restoration), with INH modification and degradation and drug resistance in *M. tuberculosis.*

The present invention also provides a kit comprising, separately packaged in association:

(a) a pair of oligonucleotide primers selected so as to amplify a portion of the DNA of the *M. tuberculosis* katG gene comprising a plurality of NciI-MspI restriction sites, i.e. 2–5 restriction sites;

(b) an amount of a restriction endonuclease such as NciI, MspI or a mixture thereof, effective to cleave the amplified portion of said DNA at the NciI-MspI restriction sites.

The present kits will also preferably comprise instruction means for carrying out the present assay, i.e., a printed package insert, tag or label, or an audio or video tape. The present kits will also preferably comprise a control DNA digest prepared by amplifying a portion of the consensus DNA of SEQ ID NO:1 (FIG. 1), that is essentially identical to the portion defined and amplified by the pair of primers, followed by digestion of the DNA with a suitable restriction endonuclease such as NciI, MspI or a mixture thereof.

Although the present invention is exemplified by the use of NciI digestion, the restriction endonuclease depicted on Table 1 can also be employed.

TABLE 1

| Specificity | RE | |
|---|---|---|
| Cuts 463-R (sensitive): | CCSGG* | CCGG |
| | NciI<br>AhaI | MspI<br>HapII<br>HpaII |
| Cuts 463-L (resistant): | CCWGG* | |
| | ApyI<br>BstNI<br>EcoRII<br>MvaI | |

*S = C or G;
W = A or T

BRIEF DESCRIPTION OF THE DRAWINGS

FIG. 1, panels A–D, depicts the consensus DNA sequence of the katG gene as the upper of the pair of sequences (61–2295) (SEQ ID NO:1). This DNA sequence data has been submitted to Gen Bank and has been assigned accession number UO6262. The lower of the pair of sequences depicts nucleotide sequence 1970-4190 of the KpnI fragment bearing the katG gene as depicted in FIG. 6 of Institut Pasteur et al. (published PCT application WO 93/22454). This sequence (SEQ ID NO:2) has been deposited in the EMBL data library under accession number X68081 (Gen Bank X68081. gb_ba). Dots (.) above the sequence mark every tenth base. The upper sequence is in lower case in areas where variation in the sequence among isolates described hereinbelow and the consensus sequence was found. The arrow before position 70 and after position 2291 of the upper sequence indicate the sequence of the katG gene.

FIG. 2 depicts the katG amino acid consensus sequence derived from 15 strains of *M. tuberculosis* (SEQ ID NO:7).

DETAILED DESCRIPTION OF THE INVENTION

Figure 3:
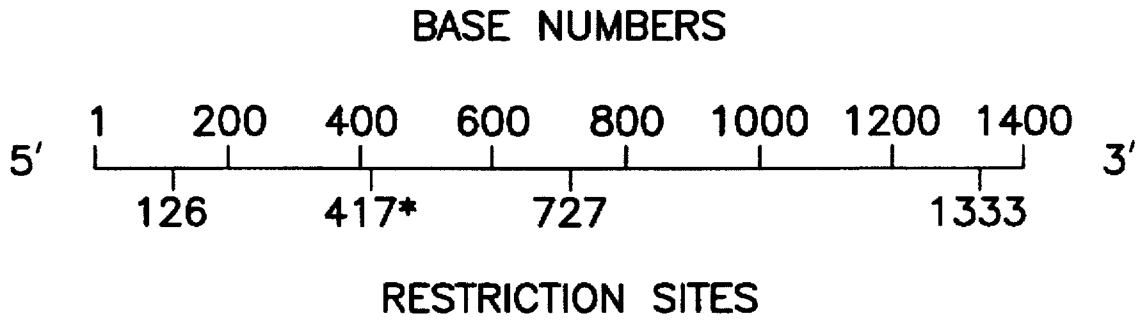
FIG. 3 schematically depicts the NciI restriction sites for the part B amplicon of katG. The (*) depicts the site of the Arg→Leu mutation which is found in some INH resistant *M. tuberculosis* strains.

Wild type strains of *M. tuberculosis* are highly susceptible to INH with minimum inhibitory INH concentration (ICmin) ≦0.02 μg/ml and a susceptible strain is considered to be one with an IC <1.0 μg/ml. At the Mayo Clinic, Rochester, Minn., clinical strains of *M. tuberculosis* (including MDR-TB strains) were identified which exhibit intermediate to high level resistance to INH (ICmin range 1.0 to >32 μg/ml). Many of these strains, especially those highly resistant to INH (≧1.0 μg/ml), exhibited diminished catalase activity as assessed by a semiquantitative technique. The mean semi-quantitative catalase was 16.5 mm for 6/15 strains with INH ICmin <1.0 μg/ml and 13.3 mm for 9/15 strains with ICmin ≧1.0 μg/ml. To develop the present assay, it was first necessary to determine whether some *M. tuberculosis* strains have decreased INH sensitivity as a result of katG gene mutations. Therefore, the nucleic acid sequences of the katG genes for both INH (ICmin <1.0 μg/ml) and INH resistant (ICmin ≧1.0 μg/ml) *M. tuberculosis* strains were determined. From the DNA sequencing data generated, a katG consensus sequence was derived, and katG sequences from all 15 *M. tuberculosis* strains (INH sensitive and INH resistant) were compared to the consensus sequence to determine katG deviations. These data in turn revealed a common restriction fragment polymorphism (RFLP) in nearly half (44%) of the 43 INH resistant strains examined.

Five of nine INH resistant strains (INH ICmin ≧1.0 μg/ml) had one or more missense mutations; one had a nonsense mutation; one had an 8 base pair deletion and one had no mutations in the coding sequences. All of the five strains with missense mutations had a common G to T transversion in the 463 codon causing replacement of arginine with leucine and loss of an NciI-MspI restriction site. Six INH sensitive strains (INH ICmin <1.0 μg/ml) were also sequenced and found to have from none to 11 amino acid differences with the consensus sequence of all 15 strains, but none of the mutations affected codon 463 or its overlapping restriction site. Restriction analysis of a total of 32 sensitive and 43 resistant strains, showed that 19 of 43 (44%) of all INH resistant strains had lost the NciI-MspI restriction site at the locus of codon 463 while only 1 of 32 sensitive strains had this restriction polymorphism.

These results indicate that the mutation, arginine→leucine, in the codon 463 of the *M. tuberculosis* catalase-peroxidase (katG) gene occurs in a significant fraction (44%) of INH resistant *M. tuberculosis* strains (INH ICmin ≧1.0 μg/ml). Furthermore, this mutation can be determined using a rapid relatively simple method, i.e., PCR amplification, digestion and monitoring for a loss of an NciI-MspI restriction site by RFLP, as described in detail hereinbelow. Although in a preferred embodiment of the invention, the number and location of the fragments is determined by gel electrophoresis, the presence or absence in the digest of a fragment comprising the NciI-MspI restriction can be determined by other methods known to the art, including immunoassays (dot blots and reverse dot blots), DNA probes, microtiter well capture and the like.

The present invention will be further described by reference to the following detailed examples, wherein 58 clinical strains of *Mycobacterium tuberculosis* were obtained from the Mycobacteriology Laboratory at the Mayo Clinic, Rochester, Minn., and 17 *M. tuberculosis* DNA preparations were obtained from the GWL Hansen's Disease Center, Louisiana State University, Baton Rouge, La. The strain designated H37Rv MC has been maintained at the Mayo Clinic for over 50 years, and therefore was isolated before INH became available as a treatment modality for tuberculosis (circa 1952). H37Rv was deposited in the American Type Tissue Collection, Rockville, Md. in 1937 by A. Karlson of the Mayo Clinic under the accession number ATCC 25618, and has been freely available to the scientific community since. An apparent variant of this strain is disclosed in PCT WO 93/22454 (SEQ ID NO:2, herein). The ATCC strains 27294 and 25618 were recovered from the same patient in 1905 and 1934, respectively. All clinical *M. tuberculosis* strains were confirmed as *M. tuberculosis* using routine identification techniques described by J. A. Washington, "Mycobacteria and Norcardia," in: *Laboratory Procedures in Clinical Microbiology*, 2d ed., Springer-Verlag, NY (1985) at pages 379–417.

For the 15 *M. tuberculosis* strains for which complete katG DNA sequencing was performed, susceptibility testing was done at the Mayo Clinic using Middlebrook 7H11 agar (DiMed, Inc., St. Paul, Minn. 55113) and the 1% proportion method described in *Manual of Clinical Microbiology*, 5th ed., A. Balows et al., eds., *Amer. Soc. Microbial.* (1991) at pages 1138–52. The same method was used at the Mayo Clinic to determine susceptibility for an additional 43 *M. tuberculosis* strains for which restriction fragment length polymorphisms (RFLP) were determined. Isoniazid concentrations tested using this method included: 0.12, 0.25, 1.0, 2, 4, 8, 16, 32 μg/ml for the 15 strains sequenced and 1.0 and 4.0 μg/ml for th eremaining 45 strains. Isoniazid resistance was defined as a maximum inhibitory concentration (ICmin) ≧1.0 μg/ml. Susceptibility testing was performed elsewhere for an additional 17 *M. tuberculosis* strains for which DNA lysates were provided by Diana L. Williams, Baton Route, La. These strains were of diverse geographical origin. 10 of these 17 strains, originated from Japan. The remaining 7 *M. tuberculosis* INH resistant strains included multiple drug resistant strains from recent MDR-TB nosocomial epidemics in New York, N.Y. and Newark, N.J. All were INH resistant (ICmin ≧1.0 μg/ml), and had resistance to at least one other drug. For all strains provided by Williams, the 1% direct proportion method was used, but the concentration of INH tested, and the media used varied as to site.

To conduct a semiquantitative test of catalase activity, *M. tuberculosis* strains were propagated on Lowenstein-Jensen media deeps contained in 20×150 mm screw-capped tubes. One ml of a 30% hydrogen peroxide (EM, Science, Gibbstown, N.Y. 08027) and 10% Tween 80 (Aldrich Chemical Co., Milwaukee, Wis. 53233) solution mixed in a 1:1 ratio was applied to the surface of growth. After 5 minutes, the highest (mm) of the column of bubbles ($O_2$) generated was recorded.

EXAMPLE 1

DNA Isolation and Polymerase Chain Reaction

For *M. tuberculosis* strains obtained from Mayo Clinic samples, DNA was extracted from cells using phenol (Boehringer Mannhaim, Indianapolis, Ind. 46250-0414) and TE (1.0M Tris HCl pH 8.0, 0.1M EDTA, Sigma, St. Louis, Mo. 63778) in a ratio of 600μl:400 μl and 0.1 mm zirconium beads (Biospec Products, Bartlesville, Okla. 74005). The mixture was processed in a mini-bead beater for 30 seconds and allowed to stand for an additional 15 minutes. Following a brief centrifugation to sediment the zirconium beads, DNA in the supernatant was extracted using the IsoQuick kit (MicroProbe Corp., Garden Grove, Calif. 92641).

The DNA sequence for katG (EMBL no. X6808124) employed to design primers is depicted in FIG. 1 (A–D), lower strand. The PCR method of R. K. Saiki et al., *Science*, 239, 487 (1988) was used to amplify the katG gene (ca. 2220 base pairs) in two segments which were designated A and B. Genomic DNA preparations (2 μl) were used with primers A1 (5'

TCGGACCATAACGGCTTCCTGTTGGACGAG 3')
(SEQ ID NO: 3) and A4 (5'

AATCTGCTTCGCCGACGAGGTCGTGCTGAC 3')
(SEQ ID NO: 4) or B1 (5'

CACCCCGACGAAATGGGACAACAGTTTCCT 3')
(SEQ ID NO: 5) and B2 (5'

GGGTCTGACAAATCGCGCCGGGCAAACACC 3')
(SEQ ID NO:6).

The PCR mixture (50 μl) contained 10 mM TRIS, pH 8.3, 50 mM KCl, 1.5 mM $MgCl_2$, 0.2 mM each of dATP, dTIP, dGTP, dCTP, 1 μM of each primer pair, 10% glycerol, 1.25 units/50 μl AmpliTaq DNA polymerase (Perkin Elmer Cetus). The mixture was overlaid with mineral oil and subjected to 4 min at 95° C. followed by 50 cycles of 1 min at 94° C. and 2 min at 74° C. A 1495 base pair product from the first half of katG was generated from the A1–A4 primers and 1435 base pair product was generated with the B1–B2 primer pair.

EXAMPLE 2

DNA Sequencing and Homology Analysis

The polymerase chain reaction (PCR) products were prepared for sequencing using the Magic™ PCR Preps DNA Purification System (Promega Corp., Madison, Wis. 53711). The DNA sequences were determined in both directions using the Taq dye-deoxy terminator cycle sequencing kit and 373A DNA sequencer (Applied Biosystems, Foster City, Calif. 94404) using a series of internal sequencing primers which provided appropriate coverage of katG.

The sequence data were analyzed using version 7 of the Genetics Computer Group sequence analysis software, as disclosed by J. Devereux et al., *Nucl. Acids Res.*, 12., 387 (1984). From the 15 *M. tuberculosis* DNA sequences, a consensus sequence was derived to which all *M. tuberculosis* strains were compared. This consensus sequence is depiceed in FIG. 1 (A–D) as the upper strand, and is compared to the sequence for katG (EMBL no. X6808124), depicted as the lower strand. The two sequences have 98.6% identity, as determined by the GCG program BESTFIT. The DNA sequence data has been submitted to Gen Bank and can be referenced by the accession numbers UO6262 (H37Rv MC), UO6258 (ATCC 25618), UO6259 (ATCC 27294), UO6260 (G6108), UO6261 (H35827), UO6270 (L6627-92), UO6271 (L68372), UO6264 (L11150), UO6268 (L24204), UO6269 (L33308), UO6265 (L16980), UO6266 (L1781), UO6272 (TMC306), UO6263 (L10373), and UO6267 (L23261).

The DNA data was then translated, aligned for comparison and a consensus amino acid sequence was generated (FIG. 2) (SEQ ID NO:7).

In general, the overall sequence agreement between INH sensitive and resistant strains was very high; the only deviation are those shown in Table 2.

TABLE 2

Analysis of Catalase-Peroxidase (katG) Gene in *M. tuberculosis* Strains

| | INH resistance (μg/ml) | | Amino Acid (Codon)[b] | | | | | | | | | | | | |
|---|---|---|---|---|---|---|---|---|---|---|---|---|---|---|---|
| Strain | INH | Catalase | 2 | 10 | 18 | 19 | 53 | 65 | 66 | 90 | 126 | 128 | 169 | 224 | 243 |
| H37Rv MC | <0.12 | 20 | | | | | | | | | | | | | |
| ATCC 25618 | <0.12 | 12 | | | N—S | G—D | A—P | A—T | A—P | | | | | Q—E | |
| ATCC 27294 | 0.12 | 28 | P—S | | N—S | G—D | | | | | | | | Q—E | A—S |
| G6108 | <0.12 | 12 | | | | | | | | | | | | | |
| H35827 | 0.25 | 14 | P—S | | N—S | G—D | | A—T | A—P | | M—I | | | | A—S |
| L6627-92 | 0.5 | 13 | | | | | | | | | | R—Q | | | |
| L68372 | 1 | 8 | P—S | | N—S | | | | | | M—I | | G—A | Q—E | |
| L11150 | 8 | 28 | | | | | | | | | | | | | |
| L24204 | 8 | 36 | | | | | | | | | | | | | |
| L33308 | 8 | 15 | | | | | | | | | | | | | |
| L16980 | 16 | 15 | | | | | | | | | | | | | |
| L1781 | 32 | 5 | | | | | | | | | | | | | |
| TMC 306 | >32 | 5 | | | | | | | W*[c] | | | | | | |
| L10373 | >32 | 5 | | 8 bpd[d] | | | | | | | | | | | |
| L23261 | >32 | 5 | | | | | | | | | | | | | |
| | | Consensus | P | | N | G | A | A | A | W | M | R | G | Q | A |

| | INH resistance (μg/ml) | Cata- | Amino Acid (Codon)[b] | | | | | | | | | | | | |
|---|---|---|---|---|---|---|---|---|---|---|---|---|---|---|---|
| Strain | INH | lase | 258 | 264 | 281 | 302 | 315 | 337 | 424 | 429 | 444 | 463 | 505 | 550 | 589 | 609 |
| H37Rv MC | <0.12 | 20 | | | | | | | | | | | | | | |
| ATCC 25618 | <0.12 | 12 | | | | | | | | | | | | | | M—I |
| ATCC 27294 | 0.12 | 28 | | | | | | | A—E | P—S | | | | | | |
| G6108 | <0.12 | 12 | | | | | | | | | A—V | | | A—D | | |
| H35827 | 0.25 | 14 | N—S | A—T | | | | Y—F | | | | | | | | M—I |
| L6627-92 | 0.5 | 13 | | | | | | | | | | | | | | |
| L68372 | 1 | 8 | | A—V | A—V | | | Y—C | | | | R—L | | | | |
| L11150 | 8 | 28 | | | | S—R | S—T | | | | | | | | | |
| L24204 | 8 | 36 | | | | | | | | | | R—L | | | | |
| L33308 | 8 | 15 | | | | | | | | | | | | | | |
| L16980 | 16 | 15 | | | | | S—T | | | | | | | | | |
| L1781 | 32 | 5 | | A—T | | | | | | | | R—L | | | P—T | M—I |
| TMC 306 | >32 | 5 | | | | | | | | | | | | | | |
| L10373 | >32 | 5 | | | | | | | | | | | | | | |
| L23261 | >32 | 5 | | | | | | Y—F | | | | R—L | W—R | | | M—I |
| | | Consensus | N | A | A | S | S | Y | A | P | A | R | W | A | P | M |

*1Cmin denotes maximum inhibitory concentration, INH = isoniazid, RIF rifampin, ETHAM ethambutol, STR streptomycin, CIP ciptrofloxacin
[b]A denotes alanine, C cysteine, D aspartic acid, E glutamic acid, F phenylalanine, G glycine, I isoleucine, K lysine, L leucine, M methionine, N asparginine, P proline, Q glutamine, R arginine S serine, T threonine, V valine, H tryptophan, Y tryosine, 8 bpd 8 base pair deletion
[c]TGG→TGA (U→stop codon)
[d]base pair deletion corresponding to wild type coordinates 98–105 creates a new TAG stop codon beginning 11 bp from coordinate 97.

The data in Table 2 show that only two strains, H37Rv MC and L3308, are completely homologous to the consensus. They are INH sensitive (INH ICmin <1.0 μg/ml) and INH resistant (ICmin ≧1.0 μg/ml), respectively. All other strains listed in Table 2 had 1 to 11 differences with the consensus and there was no strong correlation between the number of differences and INH sensitivity. In fact, the INH sensitive strains had the most deviations.

In the group of INH resistant strains, the most frequent change observed was the conversion of arginine at codon 463 to leucine. This was detected in five of nine isolates examined. There was not a consistent correlation between the loss of catalase activity and INH resistance since strains L11150 and L24204 had high levels of enzymatic activity, yet were INH resistant. Moreover, several other INH resistant strains showed catalase activity near the mean activity (16.5 mm) of the sensitive strains. Two other isolates had lost the ability to make normal katG gene product due either to an eight bp deletion (L10373, semiquantitative catalase, 3 mm) or a nonsense mutation (TMC 306, semiquantitative catalase 5 mm). It was not possible to determine if, or how, any of the deviations from the consensus reported in Table 2 affect catalase activity or cause INH resistance. However, the change at codon 463 is frequent enough that is indicative of resistance.

The DNA sequence analysis indicated that the codon 463 occurs in the context of an NciI-MspI restriction site (both enzymes recognize the same site). Thus, when in the wild type sequence depicted in FIG. 1 at bases 1455–1458, CCGGG, is changed to CCTGG, it is no longer recognized (or cleaved) by either of these enzymes. The 1435 bp amplicon produced from the half of KatG gene containing codon 463 normally has five NciI-MspI restriction sites whereas the codon altered strains have only four sites, as shown in FIG. 3. The loss of the site in question causes a unique restriction fragment length polymorphism (RFLP), which can be readily adapted to assay for resistant strains, as described in Example 3, below.

EXAMPLE 3

RFLP Analysis

For restriction fragment length polymorphism (RFLP) analysis, a 1435 base pair amplimer (produced using the B1–B2 primers) representing the 3' half of the katG gene was generated using PCR and then digested with NciI or MspI (Sigma Chemical Co., St. Louis, Mo. 63178). The gene fragments were analyzed with agarose gel electrophoresis using 2% Metaphor agarose (FMC BioProducts, Richland, Me. 04811). The gel was stained with ethidium bromide and photographed. The investigator who performed all restriction digests and electrophoresis was blinded as to the INH ICmin results.

Figure 4:
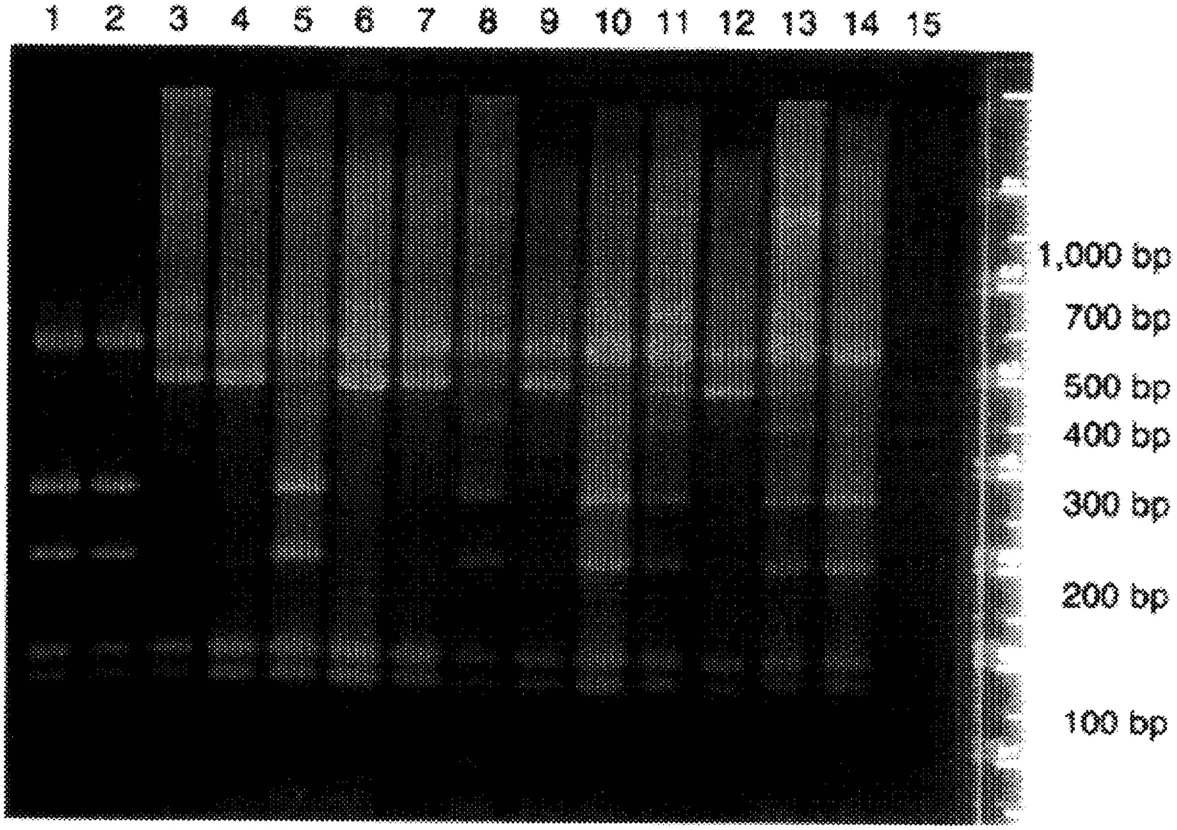
FIG. 4 depicts the results of a gel electrophoresis of the NciI digest of the part B amplicon of 14 strains of *M. tuberculosis* (1–14).

The results of this experiment are depicted in FIG. 4, wherein Lane 1 denotes strain H37Rv MC, ICmin=<0.12 μg/ml; (2) L6627-92, 0.5 μg/mL; (3) L68372, 1.0 μg/ml; (4) L16980, 16 μg/mL; (5) L39791, 16 μg/mL; (6) L1781, 32 μg/mL; (7) L9118, 4 μg/mL; (8) L11150, 8 μg/mL; (9) L24204, 8 μg/mL; (10) L68858, <0.12 μg/mL; (11) 1115A <0.12 μg/mL; (12) L23261, >32 μg/mL; (13) 1341, >32 μg/mL; (14) M10838, >32 μ/mL; (15) molecular weight standard: PCR markers (United States Biochemical Corp., Cleveland, Ohio 44122). The digests obtained from resistant strains can be readily visually detected and differentiated from digests from susceptible strains.

Subsequently, a total of 75 *M. tuberculosis* strains (including the 15 strains sequenced) were analyzed for their loss of the appropriate restriction site. Of these strains, 32 were INH sensitive and 43 were INH resistant. The data showed that 19 (44%) of the 43 resistant strains had lost the expected restriction site in codon 463. One of the 33 (2.9%) sensitive strains had lost this restriction sites as well. None of the six sensitive strains listed in Table 1 lost this site.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for determining the susceptibility of a strain of *M. tuberculosis* to isoniazid comprising employing the technique of restriction length polymorphism analysis to determine whether a NciI-MspI restriction site is absent in the DNA of said strain at the codon corresponding to codon 463 of the *M. tuberculosis* katG gene consensus sequence depicted in FIG. 1 (SEQ ID NO:1), wherein said absence is indicative of an INH-resistant strain.

2. The method of claim 1 which comprises the steps of:

(a) amplifying a portion of the katG gene of an *M. tuberculosis* isolate to yield a detectable amount of DNA comprising a plurality of NciI-MspI restriction sites;

(b) cleaving the amplified DNA with a restriction endonuclease at said sites to yield DNA fragments; and (c) employing the techniques of gel electrophoresis to determine whether the number and location of the DNA fragments is indicative of the absence of an NciI-MspI restriction site at codon 463 of said katG gene, wherein said absence is indicative of an INH resistant strain of *M. tuberculosis* in said isolate.

3. The method of claim 2 wherein the amplified DNA comprises 4 NciI-MspI restriction sites prior to cleavage.

4. The method of claim 1 wherein said DNA is amplified employing two oligonucleotide primers of the sequences (SEQ ID NO:5) and (SEQ ID NO:6) or subunits thereof, in a polymerase chain reaction to yield a 1435 base pair subunits of the katG gene.

5. The method of claim 1 wherein the technique of polymerase chain reaction (PCR) is employed to amplify DNA from the katG gene of the isolate of *M. tuberculosis* to be assayed.

6. An oligonuclcotidc selected from the group consisting of SEQ ID NO:3, SEQ ID NO:4, SEQ ID NO: 5, SEQ ID NO:6, and subunits thereof which subunits are effective for the amplification of a region incorporating codon 463 of *M. tuberculosis* katG gene.

7. The oligonucleotide of claim 6 selected from the group consisting of SEQ ID NO:3, SEQ ID NO:4, SEQ ID NO:5, and SEQ ID NO:6.

* * * * *

UNITED STATES PATENT AND TRADEMARK OFFICE

CERTIFICATE OF CORRECTION

PATENT NO.: 5,688,639
DATED: November 18, 1997
INVENTOR(S): Franklin R. Cockerill et al.

It is certified that error appears in the above-identified patent and that said Letters Patent is hereby corrected as shown below:

Title Page, Item [54], delete "RESISTENT" and insert --RESISTANT--;

Title Page, Item [56] insert

--OTHER PUBLICATIONS

D. Snider, "Research Towards Global Control and Prevention of Tuberculosis with an Emphasis on Vaccine Development," Rev. Inf. Dis., 11, S336 (1989).

R.E. Chaisson et al., "Tuberculosis in Patients with the Acquired Immunodeficiency Syndrome," Am. Res. Resp. Dis., 136, 570 (1987).

D.E. Snider, Jr., et al., "The New Tuberculosis," New Engl. J. Med., 326, No. 10, 703 (1992).

M.A. Fischl et al., "An Outbreak of Tuberculosis Caused by Multiple-Drug-resistant Tubercle Bacilli among Patients with HIV Infection," Ann. Int. Med., 117, 177 (1992).

M.L Pearson et al., "Nosocomial Transmission of Multidrug-resistant *Mycobacterium tuberculosis*. A Risk to Patients and Health Care Workers," Ann. Int. Med., 117, 191 (1992).

S.W. Dooley et al., "Multidrug-resistant Tuberculosis," Ann. Int. Med., 117, 257 (1992).

G. Middlebrook, "Isoniazid-Resistance and Catalase Activity of Tubercle Bacilli," Am. Rev. Tuberc., 69, 471 (1954).

J. Youatt, "A Review of the Action of Isoniazid," Am. Rev. Resp. Dis., 99, 729 (1969).

K. Takayama et al., "Isonicotinic Acid Hydrazide," Antibiotics, Vol. 5, *Mechanism of Action of Antibacterial Agents*, Ed. F.E. Hahn, Springer-Verlag (1979) at pp. 98-119.

Ying Zhang et al., "The catalase-peroxide gene and isoniazid resistance of *Mycobacterium tuberculosis*," Nature, 358, 591 (1992).

UNITED STATES PATENT AND TRADEMARK OFFICE

CERTIFICATE OF CORRECTION

PATENT NO.: 5,688,639
DATED: November 18, 1997
INVENTOR(S): Franklin R. Cockerill et al.

It is certified that error appears in the above-identified patent and that said Letters Patent is hereby corrected as shown below:

Ying Zhang et al., "Transformation with *katG* restores isoniazid-sensitivity in *Mycobacterium tuberculosis* isolates resistant to a range of drug concentrations," Molec. Microbiol., 8(3), 521 (1993).

B. Heym et al., "Characterization of the *katG* Gene Encoding a Catalase-Peroxidase Required for the Isoniazid Susceptibility of *Mycobacterium tuberculosis*, J. Bacteriol., 175, No. 13, 4255 (1993).

K.D. Eisenach et al., "Polymerase Chain Reaction Amplification of a Repetitive DNA Sequence Specific for *Mycobacterium tuberculosis*," J. Infect. Dis., 161, No. 4, 977 (1990).

N. Miller et al., "Evaluation of the Gen-Probe Amplified *Mycobacterium tuberculosis* Test (GPA-tb) and the Polymerase Chain Reaction (PCR) on Patients with Pulmonary Tuberculosis," Abstracts ASM, Atlanta, GA (1993) at page 177.

Sommer and Tautz, "Minimal homology requirements for PCR primers", Nucleic Acids Research, Vol. 17, No. 16, issued 1989, page 6749.--;

Col. 1, line 1, delete "RESISTENT" and insert --RESISTANT--;

Col. 1, line 30, delete "Meal" and insert --Med.--;

Col. 1, line 33, delete "Mycobacteri" and insert --Mycobacteria--;

Col. 2, line 40, delete "swain" and insert --strain--;

Col. 2, line 48, delete "swain" and insert --strain--;

Col. 4, line 57, delete "INH (ICmin" and insert --INH sensitive (ICmin--;

Col. 5, line 58, delete "Microbial." and insert --Microbiol.--;

UNITED STATES PATENT AND TRADEMARK OFFICE

CERTIFICATE OF CORRECTION

PATENT NO.: 5,688,639

DATED: November 18, 1997

INVENTOR(S): Franklin R. Cockerill et al.

It is certified that error appears in the above-identified patent and that said Letters Patent is hereby corrected as shown below:

Col. 5, line 65, delete “th eremaining” and insert --the remaining--;

Col. 6, line 54, delete “dTIP” and insert --dTTP--;

Col. 7, line 13, delete “depiceed” and insert --depicted--;

Col. 10, line 18, delete “>32 μ/mL” and insert -->32 μg/mL--;

Col. 19, line 59, delete “techniques” and insert -- technique--; and

Col. 20, line 49, delete “subunits” and insert --subunit--.

Signed and Sealed this

Twenty-ninth Day of June, 1999

*Attest:*

Q. TODD DICKINSON

*Attesting Officer* *Acting Commissioner of Patents and Trademarks*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 2235 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
AGGAATGCTG TGCCCGAGCA ACACCCACCC ATTACAGAAA CCACCACCGG AGCCGCTAGC    60
AACGGCTGTC CCGTCGTGGG TCATATGAAA TACCCCGTCG AGGGCGGCGG AAACCAGGAC   120
TGGTGGCCCA ACCGGCTCAA TCTGAAGGTA CTGCACCAAA ACCCGGCCGT CGCTGACCCG   180
ATGGGTGCGG CGTTCGACTA TGCCGCGGAG GTCGCGACCA TCGACGTTGA CGCCCTGACG   240
CGGGACATCG AGGAAGTGAT GACCACCTCG CAGCCGTGGT GGCCCGCCGA CTACGGCCAC   300
TACGGGCCGC TGTTTATCCG GATGGCGTGG CACGCTGCCG GCACCTACCG CATCCACGAC   360
```

-continued

GGCCGCGGCG GCGCCGGGGG CGGCATGCAG CGGTTCGCGC CGCTTAACAG CTGGCCCGAC 420

AACGCCAGCT TGGACAAGGC GCGCCGGCTG CTGTGGCCGG TCAAGAAGAA GTACGGCAAG 480

AAGCTCTCAT GGGCGGACCT GATTGTTTTC GCCGGCAACT GCGCGCTGGA ATCGATGGGC 540

TTCAAGACGT TCGGGTTCGG CTTCGGCCGG GTCGACCAGT GGGAGCCCGA TGAGGTCTAT 600

TGGGGCAAGG AAGCCACCTG GCTCGGCGAT GAGCGTTACA GCGGTAAGCG GGATCTGGAG 660

AACCCGCTGG CCGCGGTGCA GATGGGGCTG ATCTACGTGA ACCCGGAGGG GCCGAACGGC 720

AACCCGGACC CCATGGCCGC GGCGGTCGAC ATTCGCGAGA CGTTTCGGCG CATGGCCATG 780

AACGACGTCG AAACAGCGGC GCTGATCGTC GGCGGTCACA CTTTCGGTAA GACCCATGGC 840

GCCGGCCCGG CCGATCTGGT CGGCCCCGAA CCCGAGGCTG CTCCGCTGGA GCAGATGGGC 900

TTGGGCTGGA AGAGCTCGTA TGGCACCGGA ACCGGTAAGG ACGCGATCAC CAGCGGCATC 960

GAGGTCGTAT GGACGAACAC CCCGACGAAA TGGGACAACA GTTTCCTCGA GATCCTGTAC 1020

GGCTACGAGT GGGAGCTGAC GAAGAGCCCT GCTGGCGCTT GGCAATACAC CGCCAAGGAC 1080

GGCGCCGGTG CCGGCACCAT CCCGGACCCG TTCGGCGGGC CAGGGCGCTC CCCGACGATG 1140

CTGGCCACTG ACCTCTCGCT GCGGGTGGAT CCGATCTATG AGCGGATCAC GCGTCGCTGG 1200

CTGGAACACC CCGAGGAATT GGCCGACGAG TTCGCCAAGG CCTGGTACAA GCTGATCCAC 1260

CGAGACATGG GTCCCGTTGC GAGATACCTT GGGCCGCTGG TCCCCAAGCA GACCCTGCTG 1320

TGGCAGGATC CGGTCCCTGC GGTCAGCCAC GACCTCGTCG GCGAAGCCGA GATTGCCAGC 1380

CTTAAGAGCC AGATCCGGGC ATCGGGATTG ACTGTCTCAC AGCTAGTTTC GACCGCATGG 1440

GCGGCGGCGT CGTCGTTCCG TGGTAGCGAC AAGCGCGGCG GCGCCAACGG TGGTCGCATC 1500

CGCCTGCAGC CACAAGTCGG GTGGGAGGTC AACGACCCCG ACGGGGATCT GCGCAAGGTC 1560

ATTCGCACCC TGGAAGAGAT CCAGGAGTCA TTCAACTCCG CGGCGCCGGG GAACATCAAA 1620

GTGTCCTTCG CCGACCTCGT CGTGCTCGGT GGCTGTGCCG CCATAGAGAA AGCAGCAAAG 1680

GCGGCTGGCC ACAACATCAC GGTGCCCTTC ACCCCGGGCC GCACGGATGC GTCGCAGGAA 1740

CAAACCGACG TGGAATCCTT TGCCGTGCTG GAGCCCAAGG CAGATGGCTT CCGAAACTAC 1800

CTCGGAAAGG GCAACCCGTT GCCGGCCGAG TACATGCTGC TCGACAAGGC GAACCTGCTT 1860

ACGCTCAGTG CCCCTGAGAT GACGGTGCTG GTAGGTGGCC TGCGCGTCCT CGGGCAAACT 1920

ACAAGCGCTT ACCGCTGGGC GTGTTCACCG AGGCCTCCGA GTCACTGACC AACGACTTCT 1980

TCGTGAACCT GCTCGACATG GGTATCACCT GGGAGCCCTC GCCAGCAGAT GACGGGACCT 2040

ACCAGGGCAA GGATGGCAGT GGCAAGGTGA AGTGGACCGG CAGCCGCGTG GACCTGGTCT 2100

TCGGGTCCAA CTCGGAGTTG CGGGCGCTTG TCGAGGTCTA TGGCGCCGAT GACGCGCAGC 2160

CGAAGTTCGT GCAGGACTTC GTCGCTGCCT GGGACAAGGT GATGAACCTC GACAGGTTCG 2220

ACGTGCGCTG ATTCG 2235

( 2 ) INFORMATION FOR SEQ ID NO:2:

( i ) SEQUENCE CHARACTERISTICS:
( A ) LENGTH: 2221 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

AGGAATGCTG TGCCCGAGCA ACACCCACCC ATTACAGAAA CCACCACCGG AGCCGCTAGC 60

-continued

AACGGCTGTC CCGTCGTGGG TCATATGAAA TACCCCGTCG AGGGCGGCGG AAACCAGGAC 120

TGGTGGCCCA ACCGGCTCAA TCTGAAGGTA CTGCACCAAA ACCCGGCCGT CGCTGACCCG 180

ATGGGTGCGG CGTTCGACTA TGCCGCGGAG GTCGCGACCA GTCGACTTGA CGCCCTGACG 240

CGGGACATCG AGGAAGTGAT GACCACCTCG CAGCCGTGGT GGCCCGCCGA CTACGGCCAC 300

TACGGGCCGC TGTTTATCCG GATGGCGTGG CACGCTGCCG GCACCTACCG CATCCACGAC 360

GGCCGCGGCG GCGCCGGGGG CGGCATGCAG CGGTTCGCGC CGCTTAACAG CTGGCCCGAC 420

AACGCCAGCT TGGACAAGGC GCGCCGGCTG CTGTGGCCGG TCAAGAAGAA GTACGGCAAG 480

AAGCTCTCAT GGGCGGACCT GATTGTTTTC GCCGGCAACC GCTGCGCTCG GAATCGATGG 540

GCTTCAAGAC GTTCGGGTTC GGCTTCGGGC GTCGACCAGT GGGAGACCGA TGAGGTCTAT 600

TGGGGCAAGG AAGCCACCTG GCTCGGCGAT GACGGTTACA GCGTAAGCGA TCTGGAGAAC 660

CCGCTGGCCG CGGTGCAGAT GGGGCTGATC TACGTGAACC CGGAGGCGCC GAACGGCAAC 720

CCGGACCCCA TGGCCGCGGC GGTCGACATT CGCGAGACGT TTCGGCGCAT GGCCATGAAC 780

GACGTCGAAA CAGCGGCGCT GATCGTCGGC GGTCACACTT TCGGTAAGAC CCATGGCGCC 840

GGCCCGGCCG ATCTGGTCGG CCCCGAACCC GAGGCTGCTC CGCTGGAGCA GATGGGCTTG 900

GGCTGGAAGA GCTCGTATGG CACCGGAACC GGTAAGGACG CGATCACCAG CGGCATCGAG 960

GTCGTATGGA CGAACACCCC GACGAAATGG GACAACAGTT TCCTCGAGAT CCTGTACGGC 1020

TACGAGTGGG AGCTGACGAA GAGCCCTGCT GGCGCTTGGC AATACACCGC CAAGGACGGC 1080

GCCGGTGCCG GCACCATCCC GGACCCGTTC GGCGGGCCAG GGCGCTCCCC GACGATGCTG 1140

GCCACTGACC TCTCGCTGCG GGTGGATCCG ATCTATGAGC GGATCACGCG TCGCTGGCTG 1200

GAACACCCCG AGGAATTGGC CGACGAGTTC CGCAAGGCCT GGTACAAGCT GATCCACCGA 1260

GACATGGGTC CCGTTGCGAG ATACCTTGGG CCGCTGGTCC CCAAGCAGAC CCTGCTGTGG 1320

CAGGATCCGG TCCCTGCGGT CAGCACGACC TCGTCGGCGA AGCAGATTGC CAGCCTTAAG 1380

AGCCAGATCC GGGCATCGGG ATTGACTGTC TCACAGCTAG TTTCGACCGC ATGGGCGGCG 1440

GCGTCGTCGT TCCGTGGTAG CGACAAGCGC GGCGGCGCCA ACGGTGGTCG CATCCGCCTG 1500

CAGCCACAAG TCGGGTGGGA GGTCAACGAC CCCGACGGAT CTGCGCAAGG TCATTCGCAC 1560

CCTGAAGAGA TCCAGGAGTC ATTCACTCGG CGCGGGAACA TCAAAGTGTC CTTCGCCGAC 1620

CTCGTCGTGC TCGGTGGCTG TGCGCCACTA GAGAAAGCAG CAAAGGCGGC TGGCCACAAC 1680

ATCACGGTGC CCTTCACCCC GGGCCCGCAC GATGCGTCGC AGGAACAAAC CGACGTGGAA 1740

TCCTTTGCCG TGCTGGAGCC CAAGGCAGAT GGCTTCCGAA ACTACCTCGG AAAGGGCAAC 1800

CGTTGCCGGC CGAGTACATC GCTGCTCGAC AAGGCGAACC TGCTTACGCT CAGTGCCCCT 1860

GAGATGACGG TGCTGGTAGG TGGCCTGCGC GTCCTCGGCG CAAACTACAA GCGCTTACCG 1920

CTGGGCGTGT TCACCGAGGC CTCCGAGTCA CTGACCAACG ACTTCTTCGT GAACCTGCTC 1980

GACATGGGTA TCACCTGGGA GCCCTCGCCA GCAGATGACG GGACCTACCA GGGCAAGGAT 2040

GGCAGTGGCA AGGTGAAGTG GACCGGCAGC CGCGTGGACC TGGTCTTCGG GTCCAACTCG 2100

GAGTTGCGGG CGCTTGTCGA GGTCTATGCG CCGATGACGC GGCAGGCGAA GTTCGTGACA 2160

GGATTCGTCG CTGCGTGGGA CAAGGTGATG AACCTCGACA GGTTCGACGT GCGCTGATTC 2220

G 2221

( 2 ) INFORMATION FOR SEQ ID NO:3:

( i ) SEQUENCE CHARACTERISTICS:

( A ) LENGTH: 30 base pairs ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:3:

TCGGACCATA ACGGCTTCCT GTTGGACGAG 30

(2) INFORMATION FOR SEQ ID NO:4:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

AATCTGCTTC GCCGACGAGG TCGTGCTGAC 30

(2) INFORMATION FOR SEQ ID NO:5:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

CACCCCGACG AAATGGGACA ACAGTTTCCT 30

(2) INFORMATION FOR SEQ ID NO:6:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

GGGTCTGACA AATCGCGCCG GGCAAACACC 30

(2) INFORMATION FOR SEQ ID NO:7:

(i) SEQUENCE CHARACTERISTICS:
(A) LENGTH: 740 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:7:

```
Val Pro Glu Gly His Pro Pro Ile Thr Glu Thr Thr Thr Gly Ala Ala
1               5                   10                  15

Ser Asn Gly Cys Pro Val Val Gly His Met Lys Tyr Pro Val Glu Gly
            20                  25                  30

Gly Gly Asn Gln Asp Trp Trp Pro Asn Arg Leu Asn Leu Lys Val Leu
        35                  40                  45

His Gln Asn Pro Ala Val Ala Asp Pro Met Gly Ala Ala Phe Asp Tyr
    50                  55                  60

Ala Ala Glu Val Ala Thr Ile Asp Val Asp Ala Leu Thr Arg Asp Ile
```

-continued

```
65                  70                  75                  80

Glu Glu Val Met Thr Thr Ser Gln Pro Trp Trp Pro Ala Asp Tyr Gly
                85                  90                  95

His Tyr Gly Pro Leu Phe Ile Arg Met Ala Trp His Ala Ala Gly Thr
            100                 105                 110

Tyr Arg Ile His Asp Gly Arg Gly Gly Ala Gly Gly Gly Met Gln Arg
        115                 120                 125

Phe Ala Pro Leu Asn Ser Trp Pro Asp Asn Ala Ser Leu Asp Lys Ala
    130                 135                 140

Arg Arg Leu Leu Trp Pro Val Lys Lys Lys Tyr Gly Lys Lys Leu Ser
145                 150                 155                 160

Trp Ala Asp Leu Ile Val Phe Ala Gly Asn Cys Ala Leu Glu Ser Met
                165                 170                 175

Gly Phe Lys Thr Phe Gly Phe Gly Phe Gly Arg Val Asp Gln Trp Glu
            180                 185                 190

Pro Asp Glu Val Tyr Trp Gly Lys Glu Ala Thr Trp Leu Gly Asp Glu
        195                 200                 205

Arg Tyr Ser Gly Lys Arg Asp Leu Glu Asn Pro Leu Ala Ala Val Gln
    210                 215                 220

Met Gly Leu Ile Tyr Val Asn Pro Glu Gly Pro Asn Gly Asn Pro Asp
225                 230                 235                 240

Pro Met Ala Ala Ala Val Asp Ile Arg Glu Thr Phe Arg Arg Met Ala
                245                 250                 255

Met Asn Asp Val Glu Thr Ala Ala Leu Ile Val Gly Gly His Thr Phe
            260                 265                 270

Gly Lys Thr His Gly Ala Gly Pro Ala Asp Leu Val Gly Pro Glu Pro
        275                 280                 285

Glu Ala Ala Pro Leu Glu Gln Met Gly Leu Gly Trp Lys Ser Ser Tyr
    290                 295                 300

Gly Thr Gly Thr Gly Lys Asp Ala Ile Thr Ser Gly Ile Glu Val Val
305                 310                 315                 320

Trp Thr Asn Thr Pro Thr Lys Trp Asp Asn Ser Phe Leu Glu Ile Leu
                325                 330                 335

Tyr Gly Tyr Glu Trp Glu Leu Thr Lys Ser Pro Ala Gly Ala Trp Gln
            340                 345                 350

Tyr Thr Ala Lys Asp Gly Ala Gly Ala Gly Thr Ile Pro Asp Pro Phe
        355                 360                 365

Gly Gly Pro Gly Arg Ser Pro Thr Met Leu Ala Thr Asp Leu Ser Leu
    370                 375                 380

Arg Val Asp Pro Ile Tyr Glu Arg Ile Thr Arg Arg Trp Leu Glu His
385                 390                 395                 400

Pro Glu Glu Leu Ala Asp Glu Phe Ala Lys Ala Trp Tyr Lys Leu Ile
                405                 410                 415

His Arg Asp Met Gly Pro Val Ala Arg Tyr Leu Gly Pro Leu Val Pro
            420                 425                 430

Lys Gln Thr Leu Leu Trp Gln Asp Pro Val Pro Ala Val Ser His Asp
        435                 440                 445

Leu Val Gly Glu Ala Glu Ile Ala Ser Leu Lys Ser Gln Ile Arg Ala
    450                 455                 460

Ser Gly Leu Thr Val Ser Gln Leu Val Ser Thr Ala Trp Ala Ala Ala
465                 470                 475                 480

Ser Ser Phe Arg Gly Ser Asp Lys Arg Gly Gly Ala Asn Gly Gly Arg
                485                 490                 495
```

-continued

| | | | | | | | | | | | | | | | |
|---|---|---|---|---|---|---|---|---|---|---|---|---|---|---|---|
| Ile | Arg | Leu | Gln | Pro | Gln | Val | Gly | Trp | Glu | Val | Asn | Asp | Pro | Asp | Gly |
| | | | 500 | | | | | 505 | | | | | 510 | | |
| Asp | Leu | Arg | Lys | Val | Ile | Arg | Thr | Leu | Glu | Glu | Ile | Gln | Glu | Ser | Phe |
| | | 515 | | | | | 520 | | | | | 525 | | | |
| Asn | Ser | Ala | Ala | Pro | Gly | Asn | Ile | Lys | Val | Ser | Phe | Ala | Asp | Leu | Val |
| | 530 | | | | | 535 | | | | | 540 | | | | |
| Val | Leu | Gly | Gly | Cys | Ala | Ala | Ile | Glu | Lys | Ala | Ala | Lys | Ala | Ala | Gly |
| 545 | | | | | 550 | | | | | 555 | | | | | 560 |
| His | Asn | Ile | Thr | Val | Pro | Phe | Thr | Pro | Gly | Arg | Thr | Asp | Ala | Ser | Gln |
| | | | | 565 | | | | | 570 | | | | | 575 | |
| Glu | Gln | Thr | Asp | Val | Glu | Ser | Phe | Ala | Val | Leu | Glu | Pro | Lys | Ala | Asp |
| | | | 580 | | | | | 585 | | | | | 590 | | |
| Gly | Phe | Arg | Asn | Tyr | Leu | Gly | Lys | Gly | Asn | Pro | Leu | Pro | Ala | Glu | Tyr |
| | | 595 | | | | | 600 | | | | | 605 | | | |
| Met | Leu | Leu | Asp | Lys | Ala | Asn | Leu | Leu | Thr | Leu | Ser | Ala | Pro | Glu | Met |
| | 610 | | | | | 615 | | | | | 620 | | | | |
| Thr | Val | Leu | Val | Gly | Gly | Leu | Arg | Val | Leu | Gly | Ala | Asn | Tyr | Lys | Arg |
| 625 | | | | | 630 | | | | | 635 | | | | | 640 |
| Leu | Pro | Leu | Gly | Val | Phe | Thr | Glu | Ala | Ser | Glu | Ser | Leu | Thr | Asn | Asp |
| | | | | 645 | | | | | 650 | | | | | 655 | |
| Phe | Phe | Val | Asn | Leu | Leu | Asp | Met | Gly | Ile | Thr | Trp | Glu | Pro | Ser | Pro |
| | | | 660 | | | | | 665 | | | | | 670 | | |
| Ala | Asp | Asp | Gly | Thr | Tyr | Gln | Gly | Lys | Asp | Gly | Ser | Gly | Lys | Val | Lys |
| | | 675 | | | | | 680 | | | | | 685 | | | |
| Trp | Thr | Gly | Ser | Arg | Val | Asp | Leu | Val | Phe | Gly | Ser | Asn | Ser | Glu | Leu |
| | 690 | | | | | 695 | | | | | 700 | | | | |
| Arg | Ala | Leu | Val | Glu | Val | Tyr | Gly | Ala | Asp | Asp | Ala | Gln | Pro | Lys | Phe |
| 705 | | | | | 710 | | | | | 715 | | | | | 720 |
| Val | Gln | Asp | Phe | Val | Ala | Ala | Trp | Asp | Lys | Val | Met | Asn | Leu | Asp | Arg |
| | | | | 725 | | | | | 730 | | | | | 735 | |
| Phe | Asp | Val | Arg | | | | | | | | | | | | |
| | | | 740 | | | | | | | | | | | | |